United States Patent [19]

Cha et al.

[11] Patent Number: 5,187,279

[45] Date of Patent: Feb. 16, 1993

[54] SYNTHESIS OF (—) SWAINSONINE AND INTERMEDIATE COMPOUNDS EMPLOYED IN SUCH SYNTHESIS

[76] Inventors: Jin K. Cha, 1030 Grassland La., Nashville, Tenn. 37220; Richard B. Bennett, III, 4102 Sir Buxton Pl., Greensboro, N.C. 27405

[21] Appl. No.: 747,391

[22] Filed: Aug. 14, 1991

Related U.S. Application Data

[63] Continuation of Ser. No. 555,523, Jul. 27, 1990, abandoned.

[51] Int. Cl.$^5$ .............. C07D 487/04; C07D 491/056; C07D 317/30
[52] U.S. Cl. .................................. 546/183; 548/565; 548/453; 549/454; 558/52; 560/183
[58] Field of Search ........................................ 546/183

[56] References Cited
PUBLICATIONS

Hajek, Chem Abs 78, 136086a (1973).
Bennett, J. Amer. Chem Soc III 2580 (1989).

*Primary Examiner*—Mark L. Berch
*Attorney, Agent, or Firm*—kane, Dalsimer, Sullivan, Kurucz, Levy, Eisele and Richard

[57] ABSTRACT

(—)-Swainsonine is prepared by the steps of first reacting a compound having the formula:

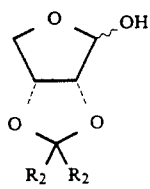

wherein each $R_2$ is lower alkyl, with (4-carbalkoxybutyl) triphenylphosphonium bromide in a strong base to obtain an alcohol having the formula:

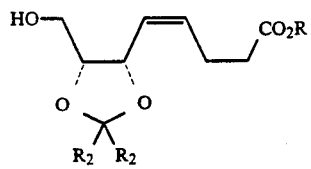

wherein $R_2$ is as defined above and R is $C_1$–$C_8$ alkyl; the alcohol is then reacted with methanesulfonyl chloride or p-toluenesulfonyl chloride or benzenesulfonyl chloride in the presence of a tertiary amine to obtain the corresponding sulfonate. Heating the sulfonate with an azide in an organic solvent yields an imine having the formula:

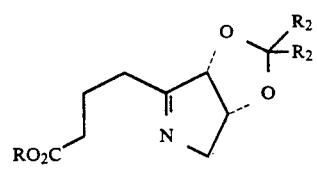

wherein $R_2$ and R are ad defined above.

Treating the imine with an inorganic base, in aqueous alcohol provides upon acidification, the corresponding acid. Heating the acid at reflux temperature in organic solvent, yields an enamide having the formula:

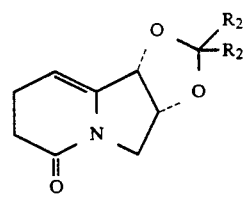

wherein $R_2$ is as defined above. Treating the enamide with diborane followed by reaction with hydrogen peroxide provides a protected swainsonine having the formula:

which upon acid hydrolysis gives swainsonine.

3 Claims, 1 Drawing Sheet

SYNTHESIS OF (—) SWAINSONINE AND INTERMEDIATE COMPOUNDS EMPLOYED IN SUCH SYNTHESIS

CROSS-REFERENCE TO RELATED APPLICATION

This application is a continuation of our U.S. application Ser. No. 555,523 filed Jul. 27 1990, and now abandoned.

The invention disclosed and claimed herein was made in the course of work under a grant from the United States Department of Health and Human Services and the United States Government has rights therein pursuant to Grant No. FM35956 awarded by the National Institutes of Health.

BACKGROUND OF THE INVENTION

1. Field of the Invention

The present invention relates to a method of synthesizing (—)-swainsonine and to unique intermediates used in such synthesis.

2. Description of the Prior Art

Swainsonine is a known compound which is a trihydroxy indolizidine alkaloid. It has been isolated from locoweed (*Astragalus lentiginosus* and *swainsona canescens*). It has also been produced from fungus (*Rhizoctonia leguminicola* and *Metarhizium anisopliae*).

the alpha-mannosidase inhibitory and immunoregulative properties of (—)-swainsonine have resulted in significant interest in biosynthetic and pharmacological studies of the compound. See, generally, Hino et al., Journal of Antibiotics Vol. 38, 926 (1985); Kino et al., Journal of Antibiotics, Vol 38, 936 (1985); Humphries et al., Proceedings of the National Academy of Sciences (USA) 83 1752 (1986); Dennis, Cancer Research 46,5131 (1986); Granato et al., Molecular Immunology 24, 849 (1987); White et al., Biochemical and Biophysical Research Communications 150, 615 (1988); and Humphries et al., Cancer Research 48, 1410 (1988).

Swainsonine also has been recognized as having potential for use in chemotherapy with cancer patients.

It has also been known to synthesize (—)-swainsonine. See, generally Fleet et al., Tetrahedron Letters 25, 1853 (1984); Ali et al., Journal of Chemical Society Communications 447 (1984); Carbohydrate , 136, 225 (1985); Suami et al., Carbohydrate , 135, 67 (1985); Yasuda et al., Chemistry Letters 1201 (1984); Adams et al., Journal of Organic Chemistry 50, 420 (1985); Setoi et al., Journal of Organic Chemistry 50, 3948 (1985); and Ikota et al., Chemical and Pharmaceutical Bulletin 35, 2140 (1987).

The known methods of synthesis, however, remain rather expensive and inefficient.

In spite of this prior knowledge, there remains a very real and substantial need for an efficient, reliable method of synthesizing swainsonine.

SUMMARY OF THE INVENTION

The need for a method of synthesizing (—)-swainsonine as set forth herein has been met by the present invention wherein a unique method of synthesis is provided as are two unique intermediate compounds.

In the preferred process of the present invention (—)-swainsonine or its analogues are synthesized by treating a material having the structure wherein
R is ($C_1$–$C_8$) alkyl;
$R_1$ is a halide or sulfonate; and
$R_2$ is
(a) ($C_1$–$C_8$) cyclic acetal (ketal) or
(b) ($C_1$–$C_8$) a±koxymetny1 or
(c) arylmethyl,
to produce an imine structure wherein
R is ($C_1$–$C_8$) alkyl; and
$R_2$ is
(a) ($C_1$–$C_8$) cyclic acetal (ketal) or
(b) ($C_1$–$C_8$) alkoxymethyl or
(c) arylmethyl.

The imine is hydrolized with an inorganic base to produce an acid which is subsequently heated at reflux temperature in a suitable organic solvent to produce an enamide of the following structure wherein
$R_2$ is
(a) ($C_1$–$C_8$) cyclic acetal (ketal) or
(b) ($C_1$–$C_8$) alkoxymethyl or
(c) arylmethyl.

$R_3$ = an oxygen atom or a hydrogen atom, and treating the enamide with borane, followed by removal of a protective group to produce swainsonine.

The imine and enamide intermediates have unique compositions.

It is an object of the present invention to provide a reliable means for synthesizing swainsonine and its analogues.

It is a further object of the present invention to provide such a method which is highly efficient and economical to employ.

It is a further object of the invention to provide a relatively simple enantioselective method of synthesizing (—)-swainsonine.

It is an object of the present invention to provide unique imine and enamide intermediates for use in such a process.

These and other objects of the invention will be more fully understood from the following description of the invention on reference to the illustrations appended hereto.

DESCRIPTION OF THE PREFERRED EMBODIMENT

In general, the present invention contemplates construction of a bicyclic imine which may be employed to create the enamide of the invention with subsequent stereospecific hydroboration of the enamide being employed to synthesize swainsonine or its analogues.

In the preferred practice of the invention a highly efficient method of synthesizing swainsonine involves protecting the 1,2-diol moiety of swainsonine as an isopropylidene group followed by removal thereof as by acidic hydrolysis.

Figure 1:
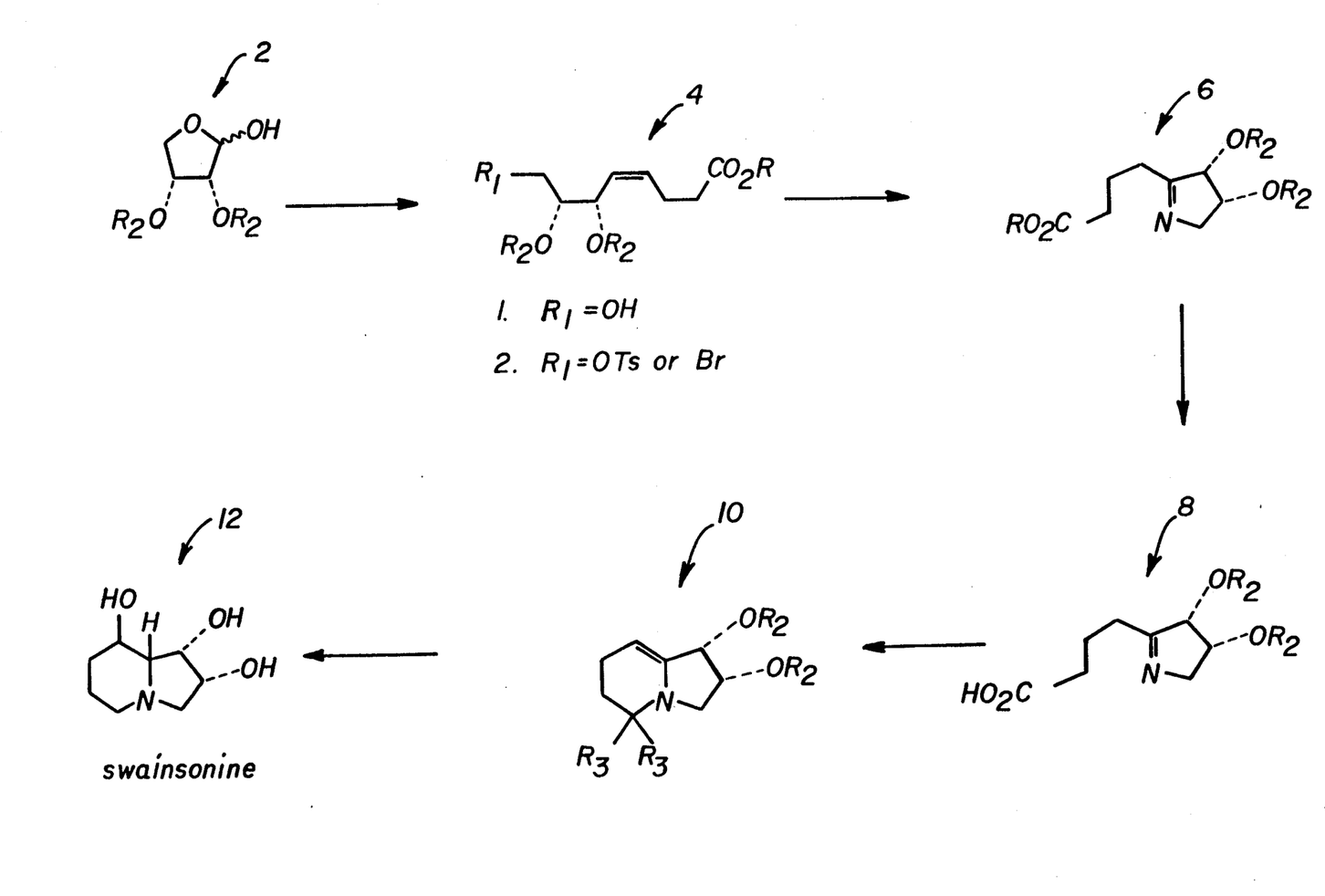
The Figure illustrates a preferred method of effecting the synthesis of the present invention.

Swainsonine $(-)(1S,2R,8R,8aR)$-1,2,8-trihydroxyoctahydroindolizine has the structure Referring to the Figure, there is shown a compound identified by the reference number 2 which is 2,3-O-isopropylidine-D-erythrose (also known as acetonide) which is a suitably protected D-erythrose. This is converted to a material 4 having the structure wherein
R is $(C_1-C_8)$ alkyl; and
$R_1$ is a halide or sulfonate. (The indication $R_1=OH$ in the Figure is for the alcohol).
$R_2$ is
  (a) $(C_1-C_8)$ cyclic acetal (ketal) or
  (b) $(C_1-C_8)$ alkoxymethyl or
  (c) arylmethyl.

Among the preferred materials for R are methyl, ethyl, propyl and benzyl.

Among the preferred materials for $R_1$ are chloride, bromide, p-toluenesulfonate, benzenesulfonate, or methanesulfonate.

Among the preferred materials for $R_2$ are (a) methylene, isopropylidene, cyclopentylidene, cyclohexylidene, benzylidene, or (b) methoxymethyl, 2-methoxyethoxymethyl, benzyloxymethyl, or (c) benzyl, p-methoxybenzyl or p-nitrobenzyl.

For example, alcohol 4 was prepared with a 50-65 percent yield by coupling 2,3,-isopropylidene-D-erythrose with the known Wittig reagent (4-carbethoxybutyl) triphenylphosphonium bromide and $KN(SiMe_3)_2$ in THF at $-78$ degrees C. to 0 degrees C. The alcohol 4 was then treated with p-toluenesulfonyl chloride to furnish the corresponding p-toluenesulfonate. This p-toluenesulfonate was treated with sodium azide $NaN_3$ in dimethyl formamide (DMF) $(CH_3)_2NCHO$ at about 70 degrees C. to 100 degrees C. to produce the imino ester 6 having the structure wherein
R is $(C_1-C_8)$ alkyl;
$R_2$ is
  (a) $(C_1-C_8)$ cyclic acetal (ketal) or
  (b) $(C_1-C_8)$ alkoxymethyl or
  (c) arylmethyl.

Examples of R are methyl, ethyl, propyl, or benzyl.

Among the preferred materials for $R_2$ are (a) methylene, isopropylidene, cyclopentylidene, cyclohexylidene, benzylidene, or (b) methoxymethyl, 2-methoxyethoxymethyl, benzyloxymethyl, or (c) benzyl, p-methoxybenzyl or p-nitrobenzyl.

By hydrolizing the imino ester 6 with an inorganic base such as $K_2CO_3$ in aqueous methyl alcohol at room temperature, an acid 8 which may be a crystalline acid was prepared. In the conversion of the imino ester to the acid, the yield was 74 percent. When this acid was heated at reflux temperatures in a suitable solvent, such as toluene, there was created in 87 percent yield, the desired enamide 10 having the structure wherein
$R_2$ is
  (a) $(C_1-C_8)$ cyclic acetal (ketal) or
  (b) $(C_1-C_8)$ alkoxymethyl or
  (c) arylmethyl; and
$R_3$ is an oxygen atom or a hydrogen atom.

Examples of $R_2$ are (a) methylene, isopropylidene, cyclopentylidene, cyclohexylidene, benzylidene; or (b) methoxymethyl, 2-methoxyethoxymethyl, benzyloxymethyl; or (c) benzyl, p-methoxybenzyl or p-nitrobenzyl.

It is believed that the crystalline acid 8 undergoes internal cyclization to provide a spiro lactone which then suffers acyl group migration and subsequent dehydration. The enamide was treated with diborane in a suitable solvent such as tetrahydrofuran (THF) $(CH_2)_4O$, to produce swainsonine acetonide which has a melting point of about 101-103 degrees C. The synthesis to swainsonine 12 was completed by acid hydrolysis with 6N hydrochloric acid in THF to yield swainsonine. The yield of swainsonine was 85 percent.

In order to reaffirm the effectiveness of the process of synthesis and the intermediate imine and enamide compounds, experiments were performed.

In summary, an example of a preferred method of synthesizing swainsonine in accordance with the Figure is as follows. An enantioselective synthesis of $(-)$-swainsonine has been achieved in 7 steps from a suitably protected D-erythrose. The suitably protected D-erythrose was coupled with (4-alkoxybutyl)-triphenylphosphonium bromide in the presence of a strong base [i.e., KN(SiMe$_3$)$_2$] to give the corresponding alcohol. Treatment of the alcohol with p-toluenesulfonyl chloride, followed by the displacement of the p-toluenesulfonyloxy group with sodium azide and the concomitant 1,3-dipolar cycloaddition gave an imino ester. Subsequent mild hydrolysis of the imino ester gave the corresponding acid. When the latter was heated in a suitable organic solvent, the enamide was obtained in good yield. The preparation of swainsonine was then completed by hydroboration with diborane in THF, followed by acid hydrolysis (6N HCl, THF).

The preferred synthesis of swainsonine of the present invention is set forth in Examples I through VII. Additional procedures and materials employable in the synthesis of swainsonine are provided in Examples VIII through XXI.

In the preferred practice of the invention the 1,2-diol moiety of swainsonine is protected by an isopropylidene group (acetonide group) which is subsequently removed by acidic hydrolysis.

EXAMPLE I

As an example of the production of the starting alcohol, the production of (+)-(4R,cis)(Z)-2,2-Dimethyl-5-[4-carbethoxy-1-butenyl]-1,3-dioxolane4-methanol 4-1 will be provided.

To a solution of 4-carbethoxybutyltriphenylphosphonium bromide (19.52 g, 42.7 mmol) in anhydrous THF (50 ml) was added dropwise potassium bis(trimethylsilyl)amide [KN(SiMe$_3$)$_2$] (82 ml, 41.0 mmol) at 0 degree C. over 10 min. The resulting red solution was stirred for an additional 30 min at 0 degree C. and then cooled to −78 degrees C. A solution of 2,3-isopropylidene-D-erythrose (2.74 g, 17.09 mmol) in THF (15 ml) was added dropwise. The reaction mixture was brought to room temperature overnight, and then quenched with saturated aqueous NH$_4$CL. The product was extracted with ether, washed with brine, dried over Na$_2$SO$_4$ and concentrated in vacuo. Purification by SiO$_2$ chromatography yielded 2.55 g (58%) of 4-1, as a pale, yellow oil: [α]D$^{25}$ = +29.25° (c 3.33, CHCl$_3$); $^1$H NMR (CDCl$_3$, 300MHz) δ1.25 (t, 3H, J=7.1 Hz), 1.40 (s,3H), 1.50 (s,3H), 1.95 (t, 1H, J=5.8 Hz), 2.33-2.50 (m,4H), 3.57 (t, 2H, J=5.8 Hz), 4.13 (q, 2H, J=7.1 Hz), 4.27 (m, 1H), 5.05 (t, 1H, J=7.4 Hz), 5.53 (dd, 1H, J=7.4 & 11.0 Hz), 5.61 (m, 1m); HRMS(M-CH$_3$) 243.1233 calcd for C$_{13}$H$_{22}$O$_5$(—CH$_3$), found 243.1226.

EXAMPLE II

As an example of the requisite sulfonate, the production of (+)-(4R, cis)(Z)-2,2-Dimethyl-5-[4-carbethoxy-1-butenyl]-1,3 dioxolane-4-methanol p-toluene-sulfonate 4-2 will be provided.

To a solution of the alcohol (1.958 g, 7.57 mmol) produced by Example I in dry CH$_2$CL$_2$ (28 ml) at 0 degree C. there were added triethylamine (1.6 ml, 11.47 mmol), p-toluenesulfonyl chloride (1.64 g, 8.60 mmol) and N,N-dimethyl-4-aminopyridine (89 mg, 0.73 mmol). The mixture was stirred at room temperature for 20 h, and then diluted with ethyl acetate (200 ml). The reaction mixture was washed with H$_2$O (2×40 ml), saturated aqueous NaHCO$_3$ (2×40 ml) and brine solution (1×40 ml), dried over Na$_2$SO$_4$, and concentrated in vacuo to a yellow oil. Purification by SiO$_2$ column chromatography yielded 2.64 gm (85%) of tosylate 4-2, as a pale, yellow oil: [α]D$^{25}$ = +25.48° (c 2.41, CHCl$_3$); $^1$H NMR (CDCl$_3$, 300 MHz) δ1.26 (t, 3H, J=7.2 Hz), 1.33 (s, 3H), 1.36 (s, 3H), 2.35-2.39 (m, 4H), 2.44 (s, 3,H), 3.88 (dd, 1H, J=6.8 & 10.2 Hz), 4.01 (dd, 1H, J=4.6 & 10.2 Hz), 4.12 (q, 2H, J=7.2 Hz), 4.32 (m, 1H), 5.00 (dd, 1H, J=6.6 & 8.7 Hz), 5.35 (dd, 1H, J=8.7 & 10.4 Hz), 5.58 (m, 1H), 7.34 (d, 2H, J=8.2 Hz), 7.79 (d, 2H, J=8.2 Hz).

EXAMPLE III

As an example of production of the imino ester, the production of (−)0(2S, 3R)-Dimethyl-8-[3-carbethoxy-1-propyl]-7-aza-2,4-dioxabicylco[3.3.0]oct-7-ene 6 will be provided.

To a solution of the tosylate (122.4 mg, 0.30 mmol) produced by Example II in DMF (3 ml) was added sodium azide (98.7 mg, 1.52 mmol). The mixture was heated at 80 degrees C. for approximately 48 h under the N$_2$ atmosphere. The mixture was then diluted wit ethyl acetate (40 ml), washed with H$_2$O (3×5 ml) and brine solution (2×5 ml), dried over Na$_2$SO$_4$ column in vacuo. The product was purified by SiO$_2$ column chromatography (eluted with 1:1 hexane:ethyl acetate, R$_f$=0.21) to afford 61.2 mg (81% of the imino ester 6, as a viscous, yellow oil: [α]D$^{25}$−34.25° (c 2.73, CHCl$_3$); IR (CHCl$_3$) 1635 (s), 1720 (s) cm$^{-1}$; $^1$H NMR (CDCl$_3$, 400MHz) δ1.20 (t, 3H, J=7.1 Hz), 1.30 (s, 3H), 1.31 (s, 3H), 1.91-2.02 (m, 2H), 2.31-2.52 (m, 4H), 3.81 (br, d, 1H, A of AB q), 3.94 (d, 1H, B of AB q, J=16.9 Hz), 4.07 (q, 2H, J=7.1 Hz), 4.67 (m, 1H), 4.86 (d, 1H, J=5.7 Hz); $^{13}$C NMR (CDCl$_3$, 100 MHz) δ14.13, 20.88, 25.60, 26.80, 29.91, 33.66, 60.20, 64.63, 77.64, 86.53, 111.77, 173.13, 175.84; HRMS(M+—C$_2$H$_5$OH) 209.1052 calcd for C$_{13}$H$_{21}$NO$_4$(—C$_2$H$_5$OH), found 209.1049.

EXAMPLE IV

As an example of the production of the imino acid, the production of (−)-(2S, 3R)-Dimethyl-8-[3-carboxy-1-propyl]-7-aza -2,4-dioxabicyclo[3.3.0]oct-7-ene 8 will be produced.

The imino ester (884 mg, 3.46 mmol) produced by Example III was dissolved in 33 ml of methanol and 10 ml of water. Potassium carbonate (1.20g, 8.75 mmol) was added. The mixture was stirred at room temperature for 12h, and was concentrated in vacuo to remove MeOH. The aqueous mixture was washed with ether (1×10 ml), and then cooled to 0 degree C. After adjusting the pH of the solution to 3 with 1N HCl, the solution was saturated with solid sodium chloride. The aqueous layer was repeatedly extracted with ethyl acetate, and methylene chloride. The organic extracts were combined, dried over Na$_2$SO$_4$, and concentrated in vacuo to give 579 mg (74% yield) of acid 8, as a yellow solid: mp 105°-110° C., [α]D$^{25}$=28.46° (c=0.98, CHCl$_3$); IR (CHCl$_3$) 3510 (br), 1720 (s), 1640 (s) cm$^{-1}$; $^1$H NMR (CDCl$_3$, 300 MHz) δ1.34 (s, 6H), 1.91-2.04 (m, 2H), 2.33-2.38 (m,2H), 2.45-2.64 (m, 2H), 3.88 (br d, 1H, A of ABq), 3.98 (d, 1H, B of ABq, J=16.8 Hz), 4.72 (m, 1H), 4.95 (d, 1H, J=5.7 Hz), 9.47-9.82 (br s, 1H); $^{13}$C NMR (CDCl$_3$, 100 MHz) δ20.81, 25.53, 26.83, 29.74, 33.54, 63.53, 77.24, 86.32, 112.09, 176.31, 177.76.

EXAMPLE V

As an example of the production of the enamide, the production of (−)-(7S, 8R)-7,8-Isopropylidenedioxy-2-oxo-1 -azabicyclo[4.3.0]non-5-ene 10 will be provided.

A solution of acid 8 (355 mg, 1.56 mmole) in toluene (35 ml) was refluxed with a Dean-Stark trap for 30 h. The solution was then cooled to room temperature, and the solvent was removed in vacuo. The residue was purified by SiO$_2$ column chromatography (eluted with 1:1 hexane:ethyl acetate, $R_f=0.5$ in 10:1 $CH_2Cl_2$:MeOH) to provide 261 mg (80%) of enamide 10: $[\alpha]D^{25}= -86.70°$ (c=1.82, $CHCl_3$); IR ($CHCl_3$) 1650 (s), 1680 (sh) cm−1; 1H NMR ($CDCl_3$, 300MHz) δ1.36 (s, 3H), 1.45 (s, 3H), 2.34–2.57 (m, 4H), 3.70 (dd, 1H, J=5.5 & 13.1 Hz), 3.86 (d, 1H, J=13.1 Hz), 4.73 (br t, 1H), 5.03 (d, 1H, J=5.9 Hz), 5.24 (m, 1H); $^{13}C$ NMR ($CDCl_3$, 100MHz) δ20.85, 25.69, 27.44, 30.44, 49.95, 75.88, 79.30, 101.59, 112.76, 139.95, 168.50; HRMS(M+) 209.1052 calcd for $C_{11}H_{15}NO_3$, found 209.1047.

EXAMPLE VI

The conversion of the enamide to swainsonine acetonide, i.e., (−)-(1S,2R,8R,8aR)-1,2-isopropylidenedioxy-8-hydroxyindolizidine was achieved.

To a cold (0 degree C.) solution of enamide 10 (261 mg, 1.29 mmol) in anhydrous THF (1.6 ml) was added 5.0 ml of 1.0M $BH_3THF$ solution. The reaction was brought to room temperature overnight. The solvent was removed in vacuo, and ethanol (3 ml) was then added. To this solution were added sodium hydroxide (208 mg, 5.20 mmol) and 30% hydrogen peroxide (0.6 ml). Additional 2 ml of ethanol was added, and the mixture refluxed for 2 h. The mixture was cooled, the ethanol removed in vacuo, and the residue dissolved in 3 ml of $H_2O$. The aqueous solution was saturated with solid NaCl, then extracted five times each with ethyl acetate, and methylene chloride. The combined organic extracts were dried over $Na_2SO_4$, and concentrated in vacuo to give crude swainsonine acetonide as a colorless solid. Column ($SiO_2$) chromatography eluted with 25:1 $CH_2CL_2$:MeOH afforded 209.1 mg (79%) of the pure product (visualized with $I_2$) as a white crystal: mp 100–103; $[\alpha]D^{25}= -72.76°$ (c 0.43, MeOH); $^1H$ NMR ($CDCl_3$, 400MHz) δ1.18–1.24 (m, 1H), 1.33 (s, 3H), 1.51 (s, 3H), 1.61–1.70 (m, 4H), 1.85(m, 1H). 2.05 (m, 1H), 2.13 (dd, J=4.2 & 10.7 Hz, 1H), 2.98 (dt, J=3.2 & 10.6 Hz, 1H), 3.16 (d, J=10.7 Hz, 1H), 3.81–3.87 (m, 1H), 4.61 (dd, J=4.2 & 6.2 Hz, 1H), 4.71 (dd, J=4.6 & 6.2 Hz, 1H); $^{13}C$ NMR ($CDCl_3$, 100MHz) δ24.08, 24.81, 25.96, 33.01, 51.60, 59.88, 67.53, 73.68, 78.26, 79.17, 111.37; HRMS(M+) 2.13.1365 calcd for $C_{11}H_{19}NO_3$ found 213.1366.

EXAMPLE VII

Swainsonine acetonide was then converted to swainsonine, i.e., (−)-(1S, 2R, 8R, 8aR)-1,2,8-trihydroxyoctahydroindolizine 12.

To a solution of swainsonine acetonide (104 mg, 0.49 mmol) in THF (6.5 ml) was added 6.0 ml of 6M HCl. The colorless solution was stirred overnight at room temperature. The solvent was removed in vacuo, leaving a colorless, viscous oil. The oil was then purified by an ion exchange chromatography (Dowex-1×8). Fractions (visualized with iodine or ninhydrin) were collected and concentrated in vacuo to furnish 68.5 mg(81% yield) of swainsonine as a white solid: mp and mixed mp 140–142 C; $[\alpha]D^{25}= -75.71$ (c 2.33, MeOH); Rf=0.36 in 1-butanol:chloroform:ethanol:concentrated ammonium hydroxide (4:4:4:1); $^1H$ NMR ($D_2O$, ref. DSS, 300MHz) 4.34 (m, 1H, H-2), 4.24 (dd, $J_{1,8a}=3.7$ Hz, $J_{1,2}=6.1$ Hz, 1H, H-1), 3.78 (dd, J=3.9, 9.3 & 10.7 Hz, 1H, H-8), 2.89 (m, 1H), 2.86 (dd, J=2.6 & 11.0 Hz, 1H, H-3), 2.53 (dd, J=7.8 & 11.0 Hz, 1H, H-3'), 2.04 (m, 1H), 1.96 (m, 1H), 1.89 (dd, $J_{8a,8}=9.3$ Hz, $J_{8a,1}=3.7$ Hz, H-8a), 1.70 (m, 1H), 1.49 (m, 1H), 1.22 (m, 1H); $^{13}C$ NMR ($D_2O$, ref: $CH_3CN$, 100MHz) δ23.21, 32.51, 51.72, 60.65, 66.37, 69.08, 69.72, 72.87; HRMS(M+) 173.1052 calcd for $C_8H_{15}NO_3$, found 173.1041.

EXAMPLE VIII

Examples VIII-XIV illustrate the use of a benzyloxymethyl group to protect the 1,2-diol moiety of swainsonine.

As an example of the production of the starting material wherein the protecting group for the alcohol function, i.e., $R_2$ is ($C_1$-$C_8$) alkoxymethyl, (−)-2,3-dibenzyloxymethyl-D-erythronolactone, (−)-2,3-dibenzyloxymethyl-D-erythrose, and (6S, 7R) ethyl (Z)-6,7-dibenzyloxymethoxy-8-hydroxy-4-butenoate were produced.

To a solution of D-erythronolactone (1 equiv) in methylene chloride at 0 degree C. were added diisopropylethylamine (6 equiv) and benzyl chloromethyl ether (3 equiv). The resulting mixture was stirred overnight at room temperature, and poured into ice water. The aqueous layer was extracted three times with methylene chloride. The organic extracts were washed with water, dried with sodium sulfate, and concentrated in vacuo. Purification by $SiO_2$ column chromatography gave pure 2,3-dibenzyloxymethyl-D-erythronolactone. To the methylene chloride solution of 2,3-dibenzyloxymethyl-D-erythronolactone (1 equiv) thus obtained was added slowly DIBAL-H (1.1 equiv) at −78° C. The reaction mixture was stirred for 4h at −78 degrees C., and cautiously decomposed by the dropwise addition of methanol. The mixture was poured into a mixture of ice water and ethyl acetate. The pH of the resulting mixture was adjusted to 3 with 1N $H_2SO_4$. The aqueous layer was extracted four times with ethyl acetate. The organic extracts were washed with water, dried with sodium sulfate, and concentrated in vacuo. Purification by $SiO_2$ column chromatography gave 2,3-dibenzyloxymethyl-D-erythrose.

To a solution of 4-carbethoxybutyltriphenylphosphonium bromide (3.5 equiv) in anhydrous THF was added dropwise potassium bis(trimethylsilyl)amide [$KN(SiMe_3)_2$] (3.5 equiv) at 0 degree C. over 10 min. The resulting red solution was stirred for an additional 30 min at 0 degree C. and then cooled to −78 degrees C. A THF solution of 2,3-dibenzyloxymethyl-D-erythrose (1 equiv) thus obtained was added dropwise. The reaction mixture was brought to room temperature overnight, and then quenched with saturated aqueous $NH_4Cl$. The product was extracted with ether, washed with brine, dried over $Na_2SO_4$ and concentrated in vacuo. Purification by $SiO_2$ chromatography yielded ethyl (Z)-6,7-dibenzyloxymethoxy-8-hydroxy-4-butenoate.

EXAMPLE IX

As an example of the production of the corresponding sulfonate, (6S, 7R) ethyl (Z)-6,7-dibenzyloxymethoxy-8-P-toluenesulfonyloxy-4-butenoate was produced.

To a solution of the alcohol produced in Example VIII in dry $CH_2Cl_2$ at 0 degree C. there were added triethylamine, p-toluenesulfonyl chloride and N,N-dimethyl-4-aminopyridine (catalytic amount). The mixture was stirred overnight at room temperature, and then diluted with ethyl acetate. The reaction mixture was washed with $H_2O$, saturated aqueous $NaHCO_3$ and brine solution, dried over $Na_2SO_4$, and concentrated in vacuo to a yellow oil. Purification by $SiO_2$ column chromatography yielded the p-toluenesulfonate.

EXAMPLE X

As an example of production of the imino ester, the production of (3S, 4R)-3,4-dibenzyloxymethoxy-2-[3-carbethoxy-1-propyl]-pyrrolid-1-ene will be provided.

To a solution of the p-toluenesulfonate produced by Example IX in DMF was added sodium azide. The mixture was heated at 80 degrees C for 2 days under the $N_2$ atmosphere. The mixture was then diluted with ethyl acetate, washed with $H_2O$ and brine solution, dried over $Na_2SO_4$ and concentrated in vacuo. The product was purified by $SiO_2$ column chromatography to afford the imino ester.

EXAMPLE XI

As an example of the production of the imino acid, the production of (3S, 4R)-3,4- dibenzyloxymethoxy-2[3-carboxy-1-propyl]-pyrrolid-1-ene will be produced.

The imino ester produced by Example X was dissolved in a 3:1 mixture of methanol and water. Potassium carbonate was added. The mixture was stirred overnight at room temperature, and was concentrated in vacuo to remove MeOH. The aqueous mixture was washed with ether, and then cooled to 0 degree C. After adjusting the pH of the solution to 3 with 1N HCl, the solution was saturated with solid sodium chloride. The aqueous layer was repeatedly extracted with ethyl acetate, and methylene chloride. The organic extracts were combined, dried over $Na_2SO_4$, and concentrated in vacuo to give the acid.

EXAMPLE XII

As an example of the production of the enamide, the production of (−)-(7S, 8R)-7,8-O-dibenzyloxymethoxy-2-oxo-1-azabicyclo[4.3.0]non-5-ene will be provided.

A solution of the acid produced by Example XI in toluene was refluxed with a Dean-Stark trap for 30 h. The solution was then cooled to room temperature, and the solvent removed in vacuo. The residue was purified by $SiO_2$ column chromatography to provide the enamide.

EXAMPLE XIII

The conversion of the enamide to 1,2-dibenzyloxymethylswainsonine, i.e., (−)-(1S, 2R, 8R, 8aR)-1,2-dibenzyloxymethoxy-8-hydroxyindolizidine will be provided.

To a cold (0 degree C.) THF solution of the enamide produced in Example XII was added 1.0M $BH_3$ THF solution. The reaction was brought to room temperature overnight. The solvent was removed in vacuo, and ethanol was then added. To this solution were added sodium hydroxide and 30% hydrogen peroxide. Additional ethanol was added, and the mixture refluxed for 2 h. The mixture was cooled, the ethanol removed in vacuo, and the residue dissolved in $H_2O$. The aqueous solution was saturated with solid NaCl, then extracted five times each with ethyl acetate, and methylene chloride. The combined organic extracts were dried over $Na_2SO_4$, and concentrated in vacuo to give crude 1,2-dibenzyloxymethylswainsonine. Column ($SiO_2$) chromatography afforded the pure product (visualized with $I_2$).

EXAMPLE XIV

The conversion of 1,2-dibenzyloxymethylswainsonine to swainsonine, i.e., (−)-(1S, 2R, 8R, 8aR)-1,2,8-Trihydroxyoctahydroindolizidine will be provided.

To a 5% acetic acid - methanol solution of the protected swainsonine produced by Example XIII was added 10% Pd-C. The mixture was stirred under $H_2$ overnight, filtered through celite and concentrated in vacuo. The concentrate was then purified by ion exchange column chromatography to give swainsonine as a white solid.

EXAMPLE XV

Examples XV-XXI illustrate the use of benzyl group to protect the 1,2 diol moiety of swainsonine.

As an example of the production of the starting material wherein the protecting group for the alcohol function, i.e., $R_2$ is ($C_1$-$C_8$) arylmethyl, (−)-2,3-dibenzyl-D-erythronolactone, (−)-2,3-dibenzyl-D-erythrose, and (6S, 7R) ethyl (Z)-6,7-dibenzyloxy-8-hydroxy-4-butenoate were produced.

To a solution of D-erythronolactone (1 equiv) in N,N-dimethylformamide at 0 degree C. were added benzyl bromide (3 equiv) and silver oxide (3 equiv). The resulting mixture was stirred overnight at room temperature, and poured into saturated aqueous $NH_4Cl$. The aqueous layer was extracted three times with methylene chloride. The organic extracts were washed with water, dried with sodium sulfate, and concentrated in vacuo. Purification by $SiO_2$ column chromatography gave pure 2,3-dibenzyl-D-erythronolactone. To the methylene chloride solution of 2,3-dibenzyl-D-erythronolactone (1 equiv) thus obtained was added slowly DIBAL-H (1.1 equiv) at −78° C. The reaction mixture was stirred for 4h at −78 degrees C., and cautiously decomposed by the dropwise addition of methanol. The mixture was poured into a mixture of ice water and ethyl acetate. The pH of the resulting mixture was adjusted to 3 with 1N $H_2SO_4$. The aqueous layer was extracted four times with ethyl acetate. The organic extracts were washed with water, dried with sodium sulfate, and concentrated in vacuo. Purification by $SiO_2$ column chromatography gave 2,3-dibenzyl-D-erythrose.

To a solution of 4-carbethoxybutyltriphenylphosphonium bromide (3.5 equiv) in anhydrous THF was added dropwise potassium bis(trimethylsilyl)amide [$KN(SiMe_3)_2$] (3.5 equiv) at 0 degree C. over 10 min. The resulting red solution was stirred for an additional 30 min at 0 degree C. and then cooled to −78 degrees C. A THF solution of 2,3-dibenzyl-D-erythrose (1 equiv) thus obtained was added dropwise. The reaction mixture was brought to room temperature overnight, and then quenched with saturated aqueous $NH_4Cl$. The product was extracted with ether, washed with brine, dried over $Na_2SO_4$ and concentrated in vacuo. Purification by $SiO_2$ chromatography yielded ethyl (Z)-6,7-dibenzyloxy-8-hydroxy-4-butenoate.

EXAMPLE XVI

As an example of the production of the corresponding sulfonate, (6S, 7R) ethyl (Z)-6,7-dibenzyloxy-8-p-toluenesulfonyloxy-4-butenoate was produced.

To a solution of the alcohol produced in Example XV in dry $CH_2Cl_2$ at 0 degree C. there were added triethylamine, p-toluenesulfonyl chloride and N,N-dimethyl-4-aminopyridine (catalytic amount). The mixture was stirred overnight at room temperature, and then diluted with ethyl acetate. The reaction mixture was washed with H₂O, saturated aqueous NaHCO₃ and brine solution, dried over Na₂SO₄, and concentrated in vacuo to a yellow oil. Purification by SiO₂ column chromatography yielded the p-toluenesulfonate.

EXAMPLE XVII

As an example of production of the imino ester, the production of (3S, 4R)-3,4-dibenzyloxy-2[3-carbethoxy-1-propyl]-pyrrolid-1-ene will be provided.

To a solution of the p-toluenesulfonate produced by Example XVI in DMF was added sodium azide. The mixture was heated at 80 degrees C. for 2 days under the N₂ atmosphere. The mixture was then diluted with ethyl acetate, washed with H₂O and brine solution, dried over Na₂SO₄ and concentrated in vacuo. The product was purified by SiO₂ column chromatography to afford the imino ester.

EXAMPLE XVIII

As an example of the production of the imino acid, the production of (3S, 4R)-3,4-dibenzyloxy-2[3-carboxy-1-propyl]-pyrrolid-1-ene will be produced.

The imino ester produce by Example XVII was dissolved in a 3:1 mixture of methanol and water. Potassium carbonate was added. The mixture was stirred overnight at room temperature, and was concentrated in vacuo to remove MeOH. The aqueous mixture was washed with ether, and then cooled to 0 degree C. After adjusting the pH of the solution to 3 with 1N HCl, the solution was saturated with solid sodium chloride. The aqueous layer was repeatedly extracted with ethyl acetate, and methylene chloride. The organic extracts were combined, dried over Na₂SO₄, and concentrated in vacuo to give the acid.

EXAMPLE XIX

As an example of the production of the enamide, the production of (−)-(7S, 8R)-7,8-O-dibenzyloxy-2-oxo-1-azabicyclo[4.3.0]non-5-ene will be provided.

A solution of the acid produced by Example XVIII in toluene was refluxed with a Dean-Stark trap for 30 h. The solution was then cooled to room temperature, and the solvent removed in vacuo. The residue was purified by SiO₂ column chromatography to provide the enamide.

EXAMPLE XX

The conversion of the enamide to 1,2-dibenxylswainsonine, i.e., (−)-(1S, 2R, 8R, 8aR)-1,2-dibenzyloxymethoxy-8-hydroxyindolizidine will be provided.

To a cold (0 degree C.) THF solution of the enamide produced in Example XIX was added 1.0M BH₃·THF solution. The reaction was brought to room temperature overnight. The solvent was removed in vacuo, and ethanol was then added. To this solution were added sodium hydroxide and 30% hydrogen peroxide. Additional ethanol was added, and the mixture refluxed for 2 h. The mixture was cooled, ethanol removed in vacuo, and the residue dissolved in H₂O. The aqueous solution was saturated with solid NaCl, then extracted five times each with ethyl acetate, and methylene chloride. The combined organic extracts were dried over Na₂SO₄, and concentrated in vacuo to give crude 1,2-dibenzyl-swainsonine. Column (SiO₂) chromatography afforded the pure product (visualized with I₂).

EXAMPLE XXI

The conversion of 1,2-dibenzylswainsonine to swainsonine, i.e., (−)-(1S, 2S, 8R, 8aR)-1,2,8-Trihydroxyoctahydroindolizidine will be provided.

To a 5% acetic acid - methanol solution of the protected swainsonine produced by Example II was added 10% Pd-C. The mixture was stirred under H₂ overnight, filtered through celite and concentrated in vacuo. The concentrate was then purified by ion exchange column chromatography to give swainsonine as a white solid.

It will be appreciated therefore, that the present invention provides an efficient means for the synthesis of swainsonine employing unique imino ester and enamide intermediates. All of this is accomplished in an efficient and economical manner which is reliable and rapid.

Whereas particular embodiments of the invention have been described above for purposes of illustration, it will be appreciated by those skilled in the art that numerous variations of the details may be made without departing from the invention as described in the appended claims.

We claim:

1. The process for the preparation of swainsonine, which comprises;

A. reacting a compound having the formula:

wherein each R₂ is lower alkyl, with (4-carbalkoxybutyl) triphenylphosphonium bromide in a strong base to obtain an alcohol having the formula:

wherein R₂ is as defined above and R is C₁-C₈ alkyl;

B. reacting said alcohol with a compound selected from the group consisting of methanesulfonyl chloride, p-toluenesulfonyl chloride or benzenesulfonyl chloride in the presence of a tertiary amine to obtain the corresponding sulfonate having the formula:

wherein R₁ is a sulfonate; and R₂ and R are as defined above;

C. heating said sulfonate with an azide in an organic solvent to obtain an imine having the formula:

wherein $R_2$ and R are as defined above;

D. treating said imine with an inorganic base, in aqueous alcohol to obtain, upon acidification, the acid having the formula:

wherein $R_2$ is as defined above;

E. heating said acid at reflux temperature in organic solvent, to obtain an enamide having the formula:

wherein $R_2$ is as defined above;

F. treating said enamide with a molar excess of diborane reagent in an ether solvent, followed by reaction with hydrogen peroxide to obtain a protected swainsonine having the formula:

wherein $R_2$ is as def wherein $R_2$ is as defined above; and

G. converting said protected swainsonine to swainsonine by acid hydrolysis (when $R_2$ is $(C_1-C_8)$alkoxymethyl or benzyloxymethyl or by hydrogenation in the presence of a palladium catalyst (when $R_2$ is arylmethyl).

3. The process for the preparation of swainsonine, which comprises;

A. reacting a compound having the formula:

with (4-carbalkoxybutyl) triphenylphosphonium bromide in a strong base to obtain an alcohol having the formula:

wherein R is $C_1-C_8$ alkyl;

B. reacting said alcohol with a compound selected from the group consisting of methanesulfonyl chloride, p-toluenesulfonyl chloride or benzenesulfonyl chloride in the presence of a tertiary amine to obtain the corresponding sulfonate having the formula:

wherein $R_1$ is a sulfonate; and R is as defined above;

C. heating said sulfonate with an azide in an organic solvent to obtain the imine having the formula:

wherein R is as defined above;

D. treating said imine with an inorganic base, in aqueous alcohol to obtain, upon acidification, an acid having the formula:

E. heating said acid at reflux temperature in organic solvent, to obtain an enamide having the formula:

F. treating said enamide with a molar excess of diborane reagent in an ether solvent, followed by reaction with hydrogen peroxide to obtain a protected swainsonine having the formula:

and

G. converting said protected swainsonine to swainsonine by acid hydrolysis.

* * * * *

UNITED STATES PATENT AND TRADEMARK OFFICE
CERTIFICATE OF CORRECTION

PATENT NO. : 5,187,279
DATED : February 16, 1993
INVENTOR(S) : Jin K. Cha and Richard B. Bennett, III It is certified that error appears in the above-identified patent and that said Letters Patent is hereby corrected as shown below:

Col. 5, line 46; "(m, 1m) should read -- (m, 1H) -- .

Col. 5, line 55; "$CH_2CL_2$" should read -- $CH_2Cl_2$ -- .

Col. 6, line 9; "(-)0(2S, 3R)" should read -- (-)-(2S, 3R) -- .

Col. 6, line 16; "wit" should read -- with -- .

Col. 6, line 18; delete the word "column" and insert
         --and concentrated--.

Col. 6, line 21; "(81%" should read -- (81%) -- .

Col. 7, line 63; "(dd, J = 3.9" should read -- (ddd, J = 3.9, --

Col. 12, line 7; "Example II" should read -- Example XX -- .

Signed and Sealed this

Eleventh Day of January, 1994

Attest:

BRUCE LEHMAN

Attesting Officer        Commissioner of Patents and Trademarks